US00PP24447P2

(12) United States Plant Patent
Sakazaki

(10) Patent No.: US PP24,447 P2
(45) Date of Patent: May 13, 2014

(54) ***EVOLVULUS* PLANT NAMED 'USEVO1201'**

(50) Latin Name: *Evolvulus hybrida*
Varietal Denomination: USEVO1201

(75) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 74 days.

(21) Appl. No.: 13/507,519

(22) Filed: Jul. 5, 2012

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — C.A. Whealy

(57) ABSTRACT

A new and distinct cultivar of *Evolvulus* plant named 'USEVO1201', characterized by its compact, upright, outwardly spreading and mounding plant habit; freely branching growth habit; dense and bushy appearance; early and freely flowering habit; long flowering period; violet blue-colored flowers; and good garden performance.

1 Drawing Sheet

Botanical designation: *Evolvulus hybrida.*
Cultivar denomination: 'USEVO1201'.

BACKGROUND OF THE INVENTION

The present invention relates to a new and distinct cultivar of *Evolvulus* plant, botanically known as *Evolvulus hybrida* and hereinafter referred to by the name 'USEVO1201'.

The new *Evolvulus* plant is a product of a planned breeding program conducted by the Inventor in Higashiomi, Shiga, Japan and Bonsall, Calif. The objective of the breeding program is to create new compact *Evolvulus* plants with uniformly mounding plant habit, long flowering period and good garden performance.

The new *Evolvulus* plant originated from a cross-pollination made by the Inventor on Jul. 15, 2007 in Higashiomi, Shiga, Japan of a proprietary seedling selection of *Evolvulus hybrida* identified as code name 06E-22, not patented, as the female, or seed, parent with a proprietary seedling selection of *Evolvulus hybrida* identified as code name 05E, not patented, as the male, or pollen, parent. The new *Evolvulus* plant was discovered and selected by the Inventor as a single flowering plant within the progeny of the stated cross-pollination in a controlled environment in Bonsall, Calif. on May 23, 2008.

Asexual reproduction of the new *Evolvulus* plant by terminal cuttings in a controlled environment in Bonsall, Calif. since May 23, 2008 has shown that the unique features of this new *Evolvulus* plant are stable and reproduced true to type in successive generations.

SUMMARY OF THE INVENTION

Plants of the new *Evolvulus* have not been observed under all possible environmental conditions and various cultural practices. The phenotype may vary somewhat with variations in environmental conditions such as temperature and light intensity without, however, any variance in genotype.

The following traits have been repeatedly observed and are determined to be the unique characteristics of 'USEVO1201'.

These characteristics in combination distinguish 'USEVO1201' as a new and distinct *Evolvulus* plant:

1. Compact, upright, outwardly spreading and mounding plant habit.
2. Freely branching growth habit; dense and bushy appearance.
3. Early and freely flowering habit.
4. Long flowering period.
5. Violet blue-colored flowers.
6. Good garden performance.

The new *Evolvulus* plant can be compared to plants of the female parent selection. Plants of the new *Evolvulus* differ primarily from plants of the female parent selection in the following characteristics:

1. Plants of the new *Evolvulus* are more mounding than plants of the female parent selection.
2. Plants of the new *Evolvulus* flower earlier than plants of the female parent selection.

The new *Evolvulus* plant can be compared to plants of the male parent selection. Plants of the new *Evolvulus* differ primarily from plants of the male parent selection in flower size as plants of the new *Evolvulus* have larger flowers than plants of the male parent selection.

Plants of the new *Evolvulus* can be compared to plants of the *Evolvulus* 'American Blue', not patented. In side-by-side comparisons conducted in Bonsall, Calif., plants of the new *Evolvulus* differed primarily from plants of 'American Blue' in the following characteristics:

1. Plants of the new *Evolvulus* were more compact and mounding than plants of 'American Blue'.
2. Plants of the new *Evolvulus* flowered earlier than plants of 'American Blue'.

Plants of the new *Evolvulus* can also be compared to plants of the *Evolvulus* 'Hawaiian Blue Eyes', not patented. In side-by-side comparisons conducted in Bonsall, Calif., plants of the new *Evolvulus* differed primarily from plants of 'Hawaiian Blue Eyes' in the following characteristics:

1. Plants of the new *Evolvulus* were more compact and mounding than plants of 'Hawaiian Blue Eyes'.
2. Plants of the new *Evolvulus* were more freely branching than plants of 'Hawaiian Blue Eyes'.

3. Plants of the new *Evolvulus* flowered earlier than plants of 'Hawaiian Blue Eyes'.

BRIEF DESCRIPTION OF THE PHOTOGRAPHS

The accompanying colored photographs illustrate the overall appearance of the new *Evolvulus* plant showing the colors as true as it is reasonably possible to obtain in colored reproductions of this type. Colors in the photographs may differ slightly from the color values cited in the detailed botanical description which accurately describe the colors of the new *Evolvulus* plant.

The photograph at the bottom of the sheet comprises a side perspective view of a typical flowering plant of 'USEVO1201' grown in a container.

The photograph at the top of the sheet is a close-up view of a typical flowering plant of 'USEVO1201'.

DETAILED BOTANICAL DESCRIPTION

The aforementioned photographs and following observations, measurements and values describe plants grown during the spring in 11.4-cm containers in a polyethylene-covered greenhouse and finished in an outdoor nursery in Bonsall, Calif. During the production of the plants, day temperatures averaged 24° C. and night temperatures averaged 18° C. Plants were seven weeks old when the photographs and description were taken. In the following description, color references are made to The Royal Horticultural Society Colour Chart, 2007 Edition, except where general terms of ordinary dictionary significance are used.

Botanical classification: *Evolvulus hybrida* 'USEVO1201'.

Parentage:

*Female, or seed, parent.*—Proprietary seedling selection of *Evolvulus hybrida* identified as code name 06E-22, not patented.

*Male, or pollen, parent.*—Proprietary seedling selection of *Evolvulus hybrida* identified as code number 05E, not patented.

Propagation:

*Type.*—By terminal cuttings.

*Time to initiate roots, summer.*—About four days at temperatures ranging from 17° C. to 29° C.

*Time to initiate roots, winter.*—About six days at temperatures ranging from 17° C. to 21° C.

*Time to produce a rooted plant, summer.*—About 23 days at temperatures ranging from 17° C. to 29° C.

*Time to produce a rooted plant, winter.*—About 33 days at temperatures ranging from 17° C. to 21° C.

*Root description.*—Medium in thickness, fibrous; close to white in color.

*Rooting habit.*—Moderately freely branching; medium density.

Plant description:

*Plant and growth habit.*—Compact, upright, outwardly spreading and mounding plant habit; freely branching growth habit with about 18 lateral branches developing per plant; dense and bushy appearance; vigorous growth habit.

*Plant height.*—About 13.5 cm.

*Plant diameter.*—About 24 cm by 26 cm.

Lateral branch description:

*Length.*—About 15.6 cm.

*Diameter.*—About 2 mm.

*Internode length.*—About 1.2 cm.

*Strength.*—Strong.

*Aspect.*—Initially upright then falling outwardly.

*Texture.*—Pubescent.

*Color.*—Close to N187B.

Foliage description:

*Arrangement.*—Alternate; simple.

*Length.*—About 3.8 cm.

*Width.*—About 2.4 cm.

*Shape.*—Elliptical to slightly obovate.

*Apex.*—Broadly acute to obtuse.

*Base.*—Attenuate to obtuse.

*Margin.*—Entire.

*Texture, upper and lower surfaces.*—Pubescent.

*Venation pattern.*—Pinnate; arcuate.

*Color.*—Developing leaves, upper surface: Close to 146B. Developing leaves, lower surface: Close to 147C. Fully expanded leaves, upper surface: Close to 137A; venation, close to 137B. Fully expanded leaves, lower surface: Close to N138B; venation, close to N138C.

*Petiole.*—Length: About 3 mm. Diameter: About 1 mm. Texture, upper and lower surfaces: Pubescent. Color, upper surface: Close to 146C. Color, lower surface: Close to 147C.

Flower description:

*Flower arrangement and habit.*—Funnelform sessile flowers arranged in short condensed spikes; inflorescences terminal and axillary; freely flowering habit with potentially about 36 to 40 flowers developing per inflorescence, usually only one or two flowers per inflorescence open at a time; flowers face upright to slightly outwardly.

*Fragrance.*—None detected.

*Natural flowering season.*—Early flowering habit, plants of the new *Evolvulus* begin flowering about six to seven weeks after planting; plants flower continuously from spring until frost in California.

*Flower longevity.*—Individual flowers last about one to two days on the plant; flowers persistent, but abscise when dry.

*Inflorescence diameter.*—About 1.8 cm to 2.2 cm.

*Inflorescence height.*—About 2.5 cm to 3 cm.

*Flower diameter.*—About 2.3 cm.

*Flower length (height).*—About 1.3 cm.

*Flower throat diameter.*—About 4 mm.

*Flower buds.*—Length: About 1.3 cm. Diameter: About 4 mm. Shape: Obovate to obelliptic. Color: Close to 96C.

*Corolla.*—Arrangement: Five fused petals arranged in a funnelform shape. Petal lobe length (from throat): About 1.1 cm. Petal lobe width: About 1 cm. Petal shape: Obovate to spatulate. Petal apex: Rounded. Petal margin: Erose, ragged. Petal texture, upper surface: Smooth, glabrous; velvety. Petal texture, lower surface: Smooth, slightly pubescent. Throat texture: Smooth, glabrous. Tube texture: Slightly pubescent. Color: Petal lobe, when opening, upper surface: Close to 96A. Petal lobe, when opening, lower surface: Close to 96C. Petal lobe, fully opened, upper surface: Close to 96C; towards the throat and star pattern between petal lobes, close to 96A; venation, close to 96C; color becoming closer to 96D with development. Petal lobe, fully opened, lower surface: Close to 96D; venation, close to 96D. Throat: Close to NN155D; venation, close to NN155D. Tube: Close to NN155A; venation, close to NN155A.

*Calyx.*—Arrangement: One v-shaped calyx tube with five sepals fused towards the base and arranged in a single whorl. Sepal length: About 8 mm. Sepal width: About 1 mm. Sepal shape: Lanceolate. Sepal apex: Acuminate. Sepal margin: Entire. Sepal texture, upper surface: Smooth, glabrous. Sepal texture, lower surface: Densely pubescent. Color, upper surface: Close to 137A. Color, lower surface: Towards the apex, close to 147A; mid-section and base, close to 147C.

*Peduncles.*—Length: About 2.8 cm. Diameter: About 1.5 mm. Angle: Upright. Strength: Strong. Texture: Pubescent. Color: Close to 197C.

*Reproductive organs.*—Stamens: Quantity: About five per flower. Filament length: About 8 mm. Filament color: Close to NN155D. Anther shape: Lanceolate. Anther length: About 1.5 mm. Anther color: Close to 196D. Pollen amount: Scarce. Pollen color: Close to NN155B. Pistils: Quantity: One per flower. Pistil length: About 1.3 cm. Style length: About 4 mm. Style color: Close to NN155D. Stigma shape: Fine, bi-parted. Stigma color: Close to NN155C. Ovary color: Close to 145C. Seeds and fruits: Seed and fruit development have not been observed on plants of the new *Evolvulus*.

Garden performance: Plants of the new *Evolvulus* have been observed to have good garden performance and tolerate wind, rain and temperatures ranging from about 1° C. to about 40° C.

Pathogen & pest resistance: Plants of the new *Evolvulus* have not been observed to be resistant to pathogens and pests common to *Evolvulus* plants.

It is claimed:

1. A new and distinct *Evolvulus* plant named 'USEVO1201' as illustrated and described.

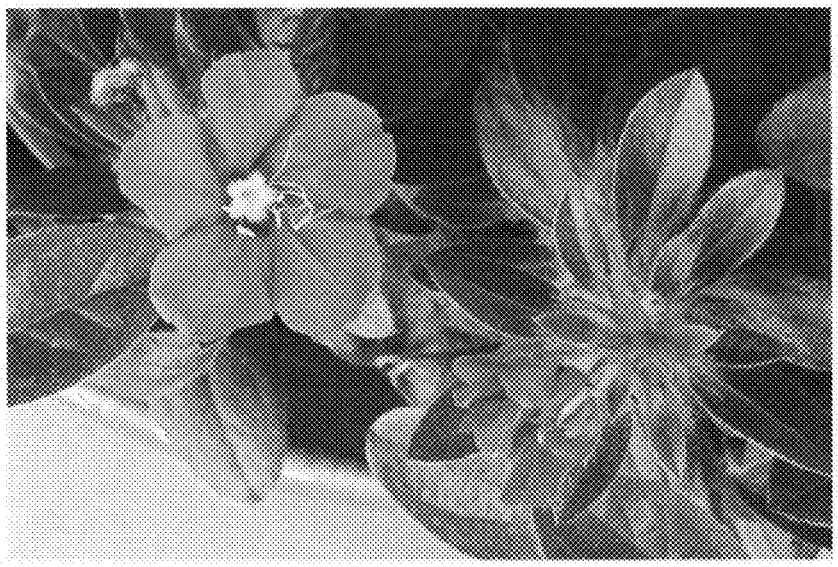
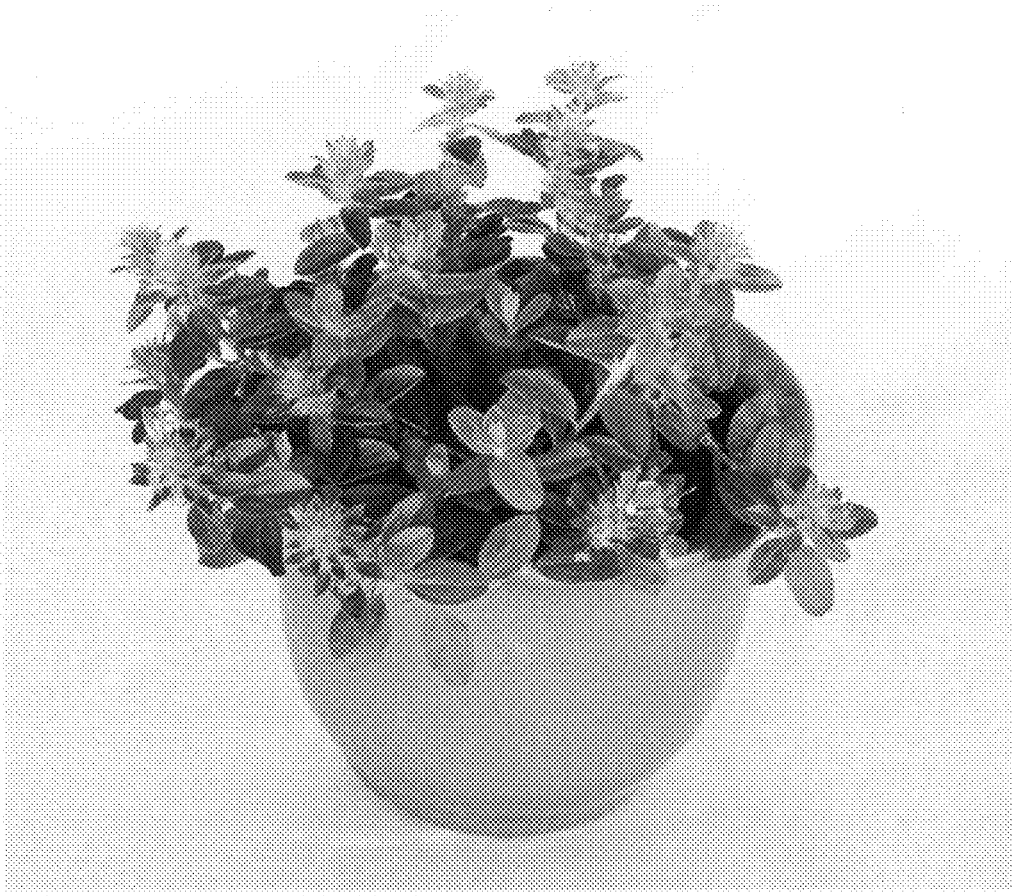

* * * * *